US009388451B2

(12) United States Patent
Ramachandran et al.

(10) Patent No.: US 9,388,451 B2
(45) Date of Patent: Jul. 12, 2016

(54) MEDICAL DEVICE DESIGN, MANUFACTURE AND TESTING SYSTEMS

(71) Applicants: Cook Biotech Incorporated, West Lafayette, IN (US); Muffin Incorporated, West Lafayette, IN (US)

(72) Inventors: Niraj Ramachandran, West Lafayette, IN (US); Frank J. Fischer, Jr., Bloomington, IN (US); Michael C. Hiles, Indianapolis, IN (US); Neal E. Fearnot, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 0 days.

(21) Appl. No.: 14/038,080

(22) Filed: Sep. 26, 2013

(65) Prior Publication Data

US 2014/0106385 A1    Apr. 17, 2014

Related U.S. Application Data

(60) Provisional application No. 61/705,650, filed on Sep. 26, 2012.

(51) Int. Cl.
| | |
|---|---|
| *C12Q 1/42* | (2006.01) |
| *G01N 33/50* | (2006.01) |
| *G01N 33/566* | (2006.01) |
| *A61M 25/00* | (2006.01) |

(52) U.S. Cl.
CPC .............. *C12Q 1/42* (2013.01); *G01N 33/5005* (2013.01); *G01N 33/5014* (2013.01); *G01N 33/566* (2013.01)

(58) Field of Classification Search
None
See application file for complete search history.

(56) References Cited

U.S. PATENT DOCUMENTS

| | | | |
|---|---|---|---|
| 5,910,287 A | 6/1999 | Cassin et al. | |
| 2005/0260557 A1* | 11/2005 | Zacour | 435/4 |
| 2006/0269445 A1* | 11/2006 | Basile | A61B 10/0096 422/400 |
| 2008/0187895 A1* | 8/2008 | Sakezles | G09B 23/306 434/268 |
| 2009/0253134 A1 | 10/2009 | Brunner et al. | |
| 2011/0150961 A1* | 6/2011 | Perry et al. | 424/411 |

FOREIGN PATENT DOCUMENTS

| | | |
|---|---|---|
| WO | WO 02/080952 A2 | 10/2002 |
| WO | WO 2007/076411 A1 | 7/2007 |
| WO | WO 2009/013484 A1 | 1/2009 |
| WO | WO 2009121565 A3 * | 2/2010 ............ A61M 31/00 |
| WO | WO 2011/150055 A2 | 12/2011 |

OTHER PUBLICATIONS

Pariente, J.L. et al. 1998. First use of cultured human urothelial cells for biocompatibility assessment: Application to urinary catheters. Journal of Biomedical Materials Research 40: 31-39. specif. pp. 31, 33, 36.*
Oxford Dictionary of Biochemistry and Molecular Biology. Lumen. Oxford University Press (publisher). Second edition. Copyright 2006. The General Editors. New York, New York. p. 394.*
Clinical Microbiology Procedures Handbook. Catheter systems. ASM Press (publisher). Third edition. Copyright 2010. Ed.: Lynne S. Garcia and Henry D. Isenberg. Washington, D.C. pp. 13.12.1-13.12.3.*
International Search Report and Written Opinion issued in PCT/US2013/061924, Jan. 3, 2014.
Poole, S. et al., A Rapid 'One-Plate' in Vitro Test for Pyrogens, Journal of Immunological Methods 274 (2003), pp. 209-220.

* cited by examiner

*Primary Examiner* — Renee Claytor
*Assistant Examiner* — Sharon M Papciak
(74) *Attorney, Agent, or Firm* — Woodard, Emhardt, Moriarty, McNett & Henry LLP

(57) ABSTRACT

Described are methods and systems for testing lumens of cannulated delivery components or assemblies thereof that may be used to deliver cells to a patient. Test cells are contacted with walls of the lumens and/or liquids that contact walls of the lumens, potentially over an incubation period. The test cells are then assessed for an effect of the wall contact, or the liquid contact, on at least one and preferably multiple characteristics of the test cells such as innate immune response, metabolic activity, viability, cytotoxic response, and/or motility. Methods and systems as described can be used in the development and/or manufacture of cannulated delivery devices, for example providing specifications for design or process inputs or outputs, design or process validations, and/or device lot approvals. Also described are devices or products produced in accordance with such methods and systems.

20 Claims, 7 Drawing Sheets

MEDICAL DEVICE DESIGN, MANUFACTURE AND TESTING SYSTEMS

REFERENCE TO RELATED APPLICATION

The present application claims the benefit of priority of U.S. Provisional Patent Application Ser. No. 61/705,650 filed Sep. 26, 2012 and entitled "Medical Device Design, Manufacture and Testing Systems", which is hereby incorporated herein by reference in its entirety.

BACKGROUND

The present invention relates generally to medical devices that may be used for cell delivery, and in certain embodiments to systems and methods by which the delivery passageways of such medical devices can be tested for their impact upon cells.

The field of cell therapy has been investigated for some time in an effort to provide improved medical treatments for patients across a broad variety of conditions or injuries. Despite some demonstrated promise in research, the clinical implementation of cell therapy has been slow. The identification of cell types and modes of administration that prove to be reliably beneficial to patients has been difficult, and the reasons for failure or only sporadic success in the clinical setting are not well known. Cells are known to be sensitive to both physical and chemical stimuli, but the identification of stimuli that may or may not benefit for detract from a proposed therapy has been limited.

In many proposed clinical applications, cells must be introduced noninvasively to the patient, and delivery devices are needed for these purposes. Little work or understanding has been reported, however, as to what specifications need be considered when developing or manufacturing delivery devices for cells in cell therapy. Critical needs thus exist in this area that take into account both the biologic sensitivities of the therapeutic agent—cell—and the complexities of medical delivery device design and manufacture. The present invention, in at least several of its aspects, is addressed to these needs.

SUMMARY

Figure 1:
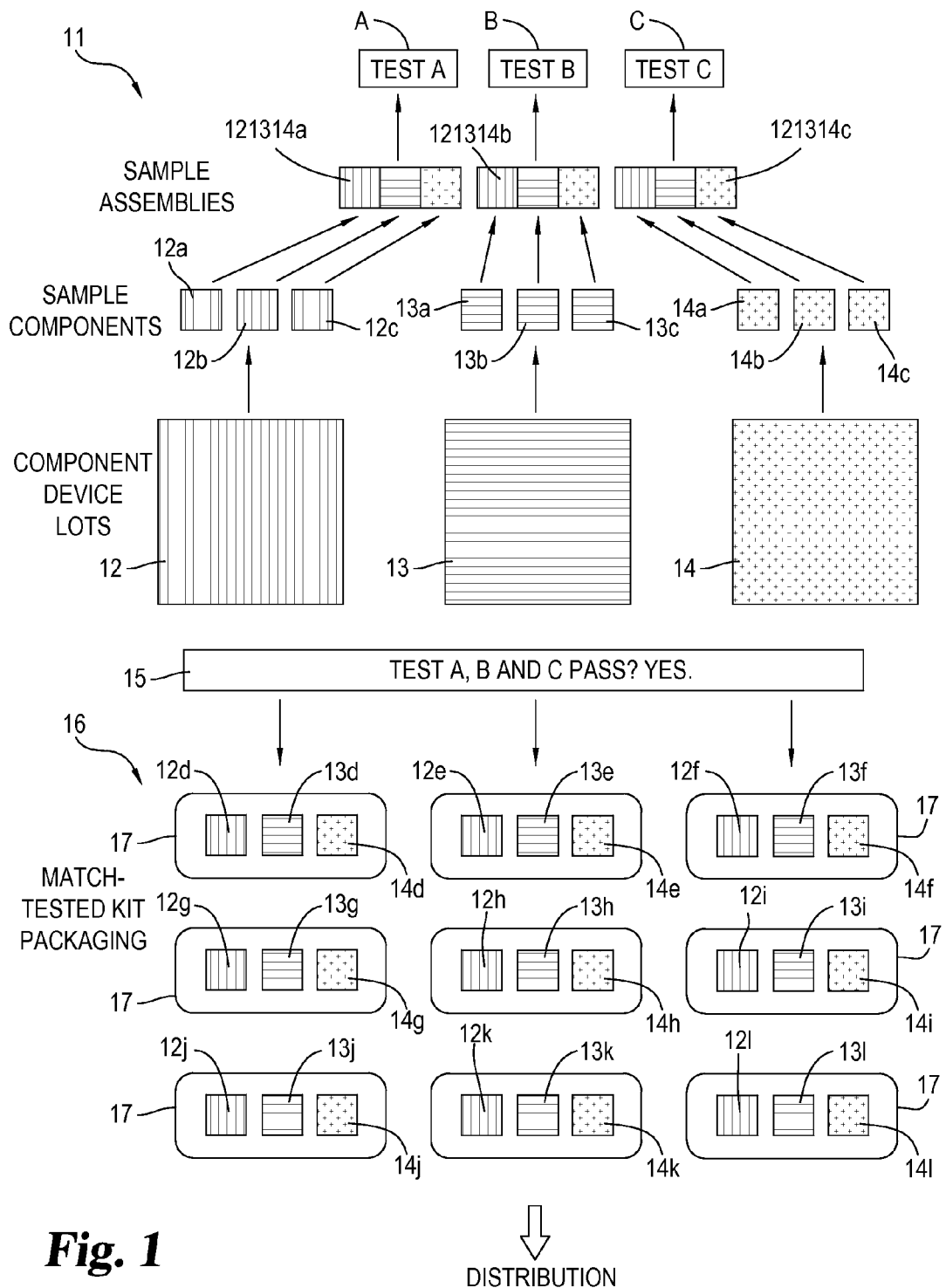
FIG. 1 provides a schematic diagram of one embodiment of a manufacturing method of the invention.

Certain aspects of the invention relate to systems and methods by which medical devices are tested for their affect on viable cells, including for example for their affect on cellular characteristics related to the performance of the cells when introduced into a human or animal patient for a therapeutic purpose. The affect may in some embodiments relate to immune response, metabolic activity, viability, cytotoxic response, proliferation, activation down an undesirable pathway, and/or migration. Sample test cells can be passed through a delivery passageway of a medical delivery device and collected. The collected cells can then be assayed to determine characteristics of the cells. The results from the collected cells can be compared to corresponding results from control cells, to determine a potential impact(s) of the medical delivery device of the cells. These methods can be used as a part of a medical device or process design or validation, and/or as a part of device lot approval. In certain embodiments the cell-based testing can be conducted on a medical delivery device that is a component assembly including at least first and second delivery components associated with one another to form the cell delivery passageway. In this fashion, the entire delivery passageway to be used by the end user can be assessed for its affect on the cells, rather than or in addition to separately assessing the component passageways. This can be used to account for potential differences in cellular effect that may occur between separate component exposure and entire passageway exposure. These differences may for example be due to contact with differing materials or surface features, connection regions between the components, or fluid stresses during flow through the entire delivery passageway.

Additional embodiments as well as features and advantages associated therewith will be apparent from the descriptions herein.

DETAILED DESCRIPTION

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

As disclosed above, aspects of the present invention relate to methods and systems for testing delivery pathways of medical delivery devices (e.g. as individual components or assemblies) that may be used to deliver cells to a patient. Test cells are contacted with walls of the lumens and/or liquid mediums that have contacted walls of the lumens, potentially over an incubation period. The test cells are then assessed for an effect of the wall contact, or the liquid medium contact, on at least one and preferably multiple characteristics of the test cells. The effect may in some embodiments pertain to immune response, metabolic activity, viability, cytotoxic response, proliferation, and/or migration. Methods and systems as described can be used in the development, manufacture and/or distribution of cannulated delivery devices, for example providing specifications for product design or process inputs, product design or process validations, and/or device lot release criteria. Also described are devices or products produced in accordance with such methods and systems, and methods for distributing the same.

Embodiments herein are useful for testing medical devices. In particular embodiments, medical delivery devices defining lumens or other pathways for the delivery of flowable materials, and especially cell-containing flowable materials such as liquids, gels or pastes, can be tested. Such delivery devices can be a single piece or can be an assembly of multiple pieces. The delivery device or devices may include one or more of a catheter having a lumen to be tested, a catheter hub having a lumen to be tested, a needle having a lumen to be tested, a needle hub having a lumen to be tested, and a syringe having a barrel to be tested. The catheter may have an expandable portion, for example as embodied in a balloon catheter. Some or all of these devices can be interconnectable with each other or with other devices, and can have adaptations for the same. Illustratively, these devices may be configured for threaded connection to one another, such as in a standard lure-lock mechanism, press-fit or other friction fit to one another, or any other suitable connection mechanism to form an assembly that provides an overall pathway for delivery of the flowable material.

The medical delivery device component(s) can be made to include any suitable material or combination of materials. Polymeric materials and metal materials are typically incorporated in such devices. Suitable polymeric materials include, for example, cellulose acetate, cellulose nitrate, silicone, cross-linked polyvinyl alcohol (PVA), polyurethane, polyamide, styrene isobutylene-styrene block copolymer (Kraton), polyethylene teraphthalate, polyester, polyorthoester, polyanhydride, polyether sulfone, polycarbonate, polypropylene, high molecular weight polyethylene, polytetrafluoroethylene, polyesters, polylactic acid or polyglycolic acid or copolymers thereof, polyanhydride, polycaprolactone, polyhydroxybutyrate valerate, or other biodegradable polymer, or mixtures or copolymers of any of these identified polymers. Suitable metals include stainless steel, nitinol, MP35N, gold, tantalum, platinum or platinum iridium, niobium, tungsten, iconel, nickel, titanium, stainless steel/titanium composites, cobalt, chromium, cobalt/chromium alloys, magnesium, aluminum, or other biocompatible metals and/or composites or alloys thereof. The walls of the medical device lumen or other delivery pathway may include any one or combination of these, or other, suitable materials.

In accordance with aspects of the invention, a sample is prepared for testing by contacting the sample in some manner with a wall or walls defining the medical device delivery pathway. In some embodiments, the sample material will contain cells as it is contacted with the walls of the pathway. The contact of such a cellular preparation with the pathway may be for any suitable incubation time and in some aspects will be for an incubation time longer that that which is expected from a typical or worst case use of the delivery pathway. This can assist in incorporating a safety factor in testing the pathway. Incubation of the sample in contact with the walls of the pathway may be done under static conditions, flow conditions, or both. Examples of static contact strategies may be found when testing for the sensitivity of the cells to a material of construction of the walls of the pathway, e.g. a polymeric material, and/or to any materials that may leach from such a material of construction. Examples in which a flowing contact of the cellular preparation with the pathway include those noted immediately above as well as testing for the tendency of cells to adhere to the pathway walls under flow conditions, as might affect the number or dose of cells finally delivered out of the pathway and into a patient. When flow conditions are used, worst case testing can be performed. This may include a worst case slow-flow testing, at a flow rate that is the lowest expected flow rate that would be employed clinically in use of the delivery pathway. For cells that may tend to adhere to the pathway walls, this may be incorporated into testing related to the released dose of cells from the pathway. Worst case high-flow testing may be conducted at a flow rate at or exceeding the maximum flow rate that would be expected to be applied during clinical use of the pathway. Because cells can be sensitive to sheer forces and other forces that may be generated during high rates of flow, this worst case testing may for example be used in testing for any impact of the delivery pathway on the performance characteristics of the cells once released from the pathway.

As noted above, the delivery pathway that is tested may be defined from a single device, or a combination of devices provided in assembly form. In such assemblies, lumens or passages in each of the devices will typically fluidly couple to another to form an overall lumen or passageway. The physical parameters of such overall passageways are determined not only by each individual passageway of the respective coupled devices, but also the regions for coupling and any gaps, ledges, changes in diameter, or other physical variations that occur at the coupling regions of the devices. These potential irregularities at coupling regions may, for example, affect the tendency of cells to be retained within the pathway even under anticipated deliver conditions e.g. by being trapped or adhered within irregularities in the pathway surface, and may also affect flow conditions to which the cells are exposed. In certain embodiments, the pathway is defined by an assembly that includes at least two of a syringe barrel, a catheter, and a needle, and potentially all three of these components. It will be understood that still other delivery devices or device components may be used either alone or in assemblies. Additionally, in certain embodiments the delivery pathway defined by the device or assembly of devices can be manipulated in a manner that would be expected during clinical use. This manipulation may for example include contact with another device, for example a guide wire, physically positioning the delivery pathway to an expected shape, e.g. a tortuous shape, expected during clinical use, or exposure of the pathway to materials or media expected during clinical use, for example exposure to blood or blood fractions in order to condition the delivery pathway with biological components as expected in use in a patient, prior to contact of the pathway with the test cells.

The delivery pathway testing will be conducted at a suitable temperature for the test undertaken. The pathway may be cooled, heated, or retained at room temperature (e.g. about 22-25° C.) during the contact of the sample to be developed for testing with the pathway. Where cellular preparations are comprised in the sample, some tests will undertake the contacting step at about physiologic temperature (about 37° C.). Any suitable arrangement for heating the delivery pathway to such temperature may be used, including for example incubators or water baths. For other sample contacts, e.g. in the absence of cells to develop the sample, temperatures lower than physiologic temperature, for example room temperature or cool temperatures, may sometimes be used.

In certain embodiments of the invention, a sample in the absence of cells is contacted with the delivery pathway. This sample can be constituted of cell culture medium. As noted above, the conditions of sample contact may be under flow, static, or combined flow and static conditions. Advantageously, in developing samples for testing in the absence of cells, long residence times within the delivery pathway can be utilized, e.g. to provide ample safety factor in the testing regimen.

In some aspects, the sample residence time in the absence of cells will exceed about 10 hours, for example in the range of about 10 hours to 48 hours. This incubation time can be sufficient to condition the sample with any impurities or other leach aids that may be released by the delivery pathway and the walls defining it, to which the cells may be sensitive. After the cell-free sample is conditioned in this manner, it can be collected from the delivery pathway for subsequent use in testing in contact with test cells. In this regard, for such cell-free samples or for cell-containing samples are discussed above, the sample volume collected from the delivery pathway can in some aspects be sufficiently large that it can be split into multiple aliquots and used in multiple tests which are the same or of differing nature.

Samples developed as discussed above or suitably otherwise will be assayed to determine whether the delivery pathway may have an affect on cells. A wide variety of cellular characteristic may be tested, including for example metabolic activity, viability, motility, proliferation, or immune affects including for instance innate or adaptive immune affects. A variety of tests for these or other cell characteristics are known and can be used. The assays for affect on cells may be qualitative or quantitative in nature, and may for example assay for the expression of proteins or transcription of DNA elements. Such expression or transcription assays may test for a selected one or group of proteins or DNA elements, or may in some instances involve an entire expression or transcription profile for the cells. Such assays may utilize intact cells (e.g. in florescence activated cell sorting), or may utilize cellular extracts such as those prepared in expression or transcription testing. Additionally, in dose testing, cell counts or estimates can be provided before and after passing a cellular preparation through the delivery pathway, in order to determine any loss of cell count experienced during passage through the delivery pathway.

Each of these tests or other determinative tests can and typically will utilize a suitable control, as is well known in the art. Controls may be positive controls, negative or null controls.

The test methods described herein may be used for a wide variety of device design, development or manufacturing purposes. Illustratively, in device design, one or more of the tests described herein may be used in the selection and testing of physical and/or materials of construction parameters for an intended delivery device. In these respects, tests described herein may be used as design or validation inputs. As well, during device development, tests as described herein may be used as specifications for design inputs or validation for devices or manufacturing processes therefor. Still further, tests as described herein may be used during manufacture of devices for commercial distribution. In one aspect, tests as described herein can be used as lot release criteria. In such embodiments, manufactured lots of devices can be isolated or quarantined until tests as described herein, designated as lot release criteria, are completed. Upon passage of the tests, the devices can be released for distribution and distributed to end users.

With reference now to FIG. 1, disclosed is one embodiment of a kit manufacturing method of the invention. In the method a manufactured lot 16 of kits is to be produced. To do so, a first lot 12 of a first component of a delivery assembly is made, along with lot 13 and lot 14 of second and third components of the delivery assembly, respectively, are manufactured. Sample components 12a-12c are taken from lot 12, sample components 13a-13c are taken from lot 13, and sample components 14a-14c are taken from lot 14. These samples are paired each with one of the samples from the other lots to create sample delivery assemblies 121314a, 121314b, and 121314c. These respective sample assemblies are subjected respectively to test A, test B, and test C as shown. These tests may for example be part of a lot release requirement for manufactured kits in lot 16. Test A, test B and test C can include any one or combination of the cell-related tests as described herein. Further, in addition to testing sample assemblies as disclosed, individual devices from lots 12, 13 and 14 may be tested singly. If the sample assemblies 121314a-c pass tests a, b and c respectively, as at determination step 15, then devices 12d-1 from lot 12, devices 13d-1 from lot 13, and devices 14d-1 from lot 14 can be packaged as shown within suitable packaging 17 and optionally terminally sterilized. In an additional potential sampling step, samples of kits from kit lot 16 may be taken, opened and the respective components combined to make additional sample assemblies, which can be subjected to cell-related testing using any one or combination of those methods described herein. Thereafter, kits from lot 16 can be released for distribution to end users.

Any one or any combination of a wide variety of cell types can be used in samples for test methods of the invention and/or as the target cell type for delivery from the medical delivery device. For example, the cells can be skin cells, skeletal muscle cells, cardiac muscle cells, lung cells, mesentery cells, or adipose cells. The adipose cells may be from omental fat, properitoneal fat, perirenal fat, pericardial fat, subcutaneous fat, breast fat, or epididymal fat. In certain embodiments, the cells comprise stromal cells, stem cells, or combinations thereof. As used herein, the term "stem cells" is used in a broad sense and includes traditional stem cells, adipose derived stem cells, progenitor cells, preprogenitor cells, reserve cells, and the like. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Additional illustrative cells which can be used include hepatocytes, epithelial cells, Kupffer cells, fibroblasts, human embryonic kidney cells, neurons, cardiomyocytes, myocytes, chondrocytes, pancreatic acinar cells, islets of Langerhans, osteocytes, myoblasts, satellite cells, endothelial cells, adipocytes, preadipocytes, biliary epithelial cells, and progentior cells of any of these cell types.

Mixtures of any of the cells identified herein, or other mixtures, may also be utilized. In certain embodiments, naturally-occurring cellular mixtures, or fractions thereof, are used. Examples of these embodiments include the use of peripheral blood or fractions thereof, bone marrow or fractions thereof, umbilical cord blood or fractions thereof, and the like.

In some embodiments, the cells are, or include, endothelial progenitor cells (EPCs). Preferred EPCs for use in the invention are endothelial colony forming cells (ECFCs), especially ECFCs with high proliferative potential. Suitable such cells are described for example in U.S. Patent Application Publication No. 20050266556 published Dec. 1, 2005, publishing U.S. patent application Ser. No. 11/055,182 filed Feb. 9, 2005, and U.S. Patent Application Publication No. 20080025956 published Jan. 1, 2008, publishing U.S. patent application Ser. No. 11/837,999, filed Aug. 13, 2007, each of which is hereby incorporated by reference in its entirety. Such ECFC cells can be a clonal population, and/or can be obtained from umbilical cord blood of humans or other animals. Additionally or alternatively, the endothelial colony forming cells have the following characteristics: (a) express the cell surface antigens CD31, CD105, CD146, and CD144; and/or (b) do not express CD45 and CD14; and/or (c) ingest acetylated LDL; and/or (d) replate into at least secondary colonies of at least 2000 cells when plated from a single cell; and/or (e) express high levels of telomerase, at least 34% of that expressed by HeLa cells; and/or (f) exhibit a nuclear to cytoplasmic ratio that is greater than 0.8; and/or (g) have cell diameters of less than about 22 microns. Any combination of some or all of these features (a)-(g) may characterize ECFCs used in the present invention.

In other embodiments, the cells are, or include, muscle derived cells, including muscle derived myoblasts and/or muscle derived stem cells. Suitable such stem cells and methods for obtaining them are described, for example, in U.S. Pat. No. 6,866,842 and U.S. Pat. No. 7,155,417, each of which is hereby incorporated herein by reference in its entirety. The muscle derived cells can express desmin, M-cadherin, MyoD, myogenin, CD34, and/or Bcl-2, and can lack expression of CD45 or c-Kit cell markers.

In still other embodiments, the cells are, or include, stem cells derived from adipose tissue. Suitable such cells and methods for obtaining them are described for example in U.S. Pat. No. 6,777,231 and U.S. Pat. No. 7,595,043, each of which is hereby incorporated herein by reference in its entirety. The cellular population can include adipose-derived stem and regenerative cells, sometimes also referred to as stromal vascular fraction cells, which can be a mixed population including stem cells, endothelial progenitor cells, leukocytes, endothelial cells, and vascular smooth muscle cells, which can be adult-derived. In certain forms, the cells can include adipose-derived cells that can differentiate into two or more of a bone cell, a cartilage cell, a nerve cell, or a muscle cell.

The cells to be used in testing can either be genetically unmodified or genetically modified cells. Genetically modified cells can include cells that have been modified to contain expressible DNA that encodes a protein or other substance of interest. The cells can then be used in tests to determine whether the cell delivery passageway has any effect (including e.g. suppression or activation) on the expression of the protein or other substance of interest. Illustratively, cells can be genetically modified by transfection or otherwise to contain exogenous DNA encoding proteins or other substances that are involved in immune response, for example toll-like receptors (TLRs), such as TLR-2, TLR-4, or TLR-7. These TLR-modified cells can then be used in testing as described herein to determine whether the delivery passageway has an effect on TLR expression by the cells.

For the purpose of promoting a further understanding of aspects of the present invention, the following Examples are provided. It will be understood that these Examples are illustrative, and not limiting, in nature.

EXAMPLE 1

Innate Immune Response Assay

This Example describes cell based assays for assessment of catheter lumens for their effect on cellular innate immune response. Specifically herein, genetically modified cells expressing TLR2 and TLR4 were used to assess catheter lumens for their potential to activate or suppress TLR2 or TLR4 expression in the cells.

Materials

Human Embryonic Kidney 293 (HEK-293) cells stably transfected with different TLR plasmids −2, −4, or −7 (TLR4 cells were also co-transfected with CD14 and MD-2) were obtained from InvivoGen (San Diego, Calif. 92121)

Cook Advance 35 LP catheters were obtained from Cook Medical, Bloomington, Ind.

Culture media for the HEK-293 cells was obtained from InvivoGen (San Diego, Calif. 92121).

Other test materials used as positive controls were tubing's of Copper and PVC. The copper tubing used was a ⅛" thick, soft refrigeration tubing bought from Kleindorfer's Hardware Store in Bloomington Ind. (Manufacturer: Cambridge-Lee Industries, Inc., Manufacturers Notice: Cleaned per ASTM B280 and NFPA 99). The PVC tubing was an 8.0 FR White manufactured by Cook Polymer Technology (Material Compound #11011, Cook Polymer Project # D-4520, Year Extruded: 2000). DMEM (negative control) was obtained from Invivogen, and PAM3CSK4 (positive control) was obtained from Imgenex.

Methods

Test Media: HEK-293 cell culture medium was incubated in contact with the 35 LP catheters and other test materials for 16 hours at room temperature (20-22° C.). For the 35 LP catheters, which were taken from a first device lot designated LOT 1, the guide wire lumen was filled completely with a volume of approximately 1 mL of the culture medium for the incubation period. For the other samples, the volume varied due to inner diameter and length of the copper (2 ml) and PVC (1.2 ml) tubes but the incubation times and temperature remained the same. (describe the incubation process). After the incubation period, the conditioned samples of culture media were collected in FACS tubes and were either for prompt use in the cellular assays.

Cell Culture:

HEK-293, TLR-2 transfected cells were plated at a concentration of 40,000 cells/well while the TLR4 transfected cells were plated at a concentration of 10,000 cells/well in separate 96 well plates. Specific media supplements were added to each cell line as directed by the cell line vendor's literature. All cytotoxicity indicator cells were incubated for 24 hours in the cell culture incubator (5% $CO_2$, 37° C.). Following this incubation period, the cell culture media was removed and replaced with the device-exposed-media. Normal cell culture media was used as a negative control. Pam3CSK4 (10 ng) and LPS (100 ug) were used as a positive controls for TLR2 and TLR4 transfected cells respectively.

NFkb Activation/Suppression Assay:

Following a 24-hour incubation period in the device or positive control modified cell culture media, a 15 µL aliquot of the cell culture supernatants was added to a 96 well microtiter plate containing 185 μL/well volume of Quick-Blue developer substrate. This substrate is used to quantitate the levels of secreted embryonic alkaline phosphatase (SEAP) enzyme activity. TLR cell lines secrete an embryonic AP enzyme form at varying levels dependent upon the amount of TLR associated signal transduction occurring as a result of the interaction of the TLR receptor with contaminants leached from devices. Activation of both the AP-1 and NF-kB proteins by the surface stimulation of the TLR type receptors leads to AP-1 and NF-kB binding to their specific binding sites on the promoter region controlling the transcription of the SEAP reporter gene. This leads to an increase in the production and export of the SEAP enzyme into the cell culture media.

Figure 2:
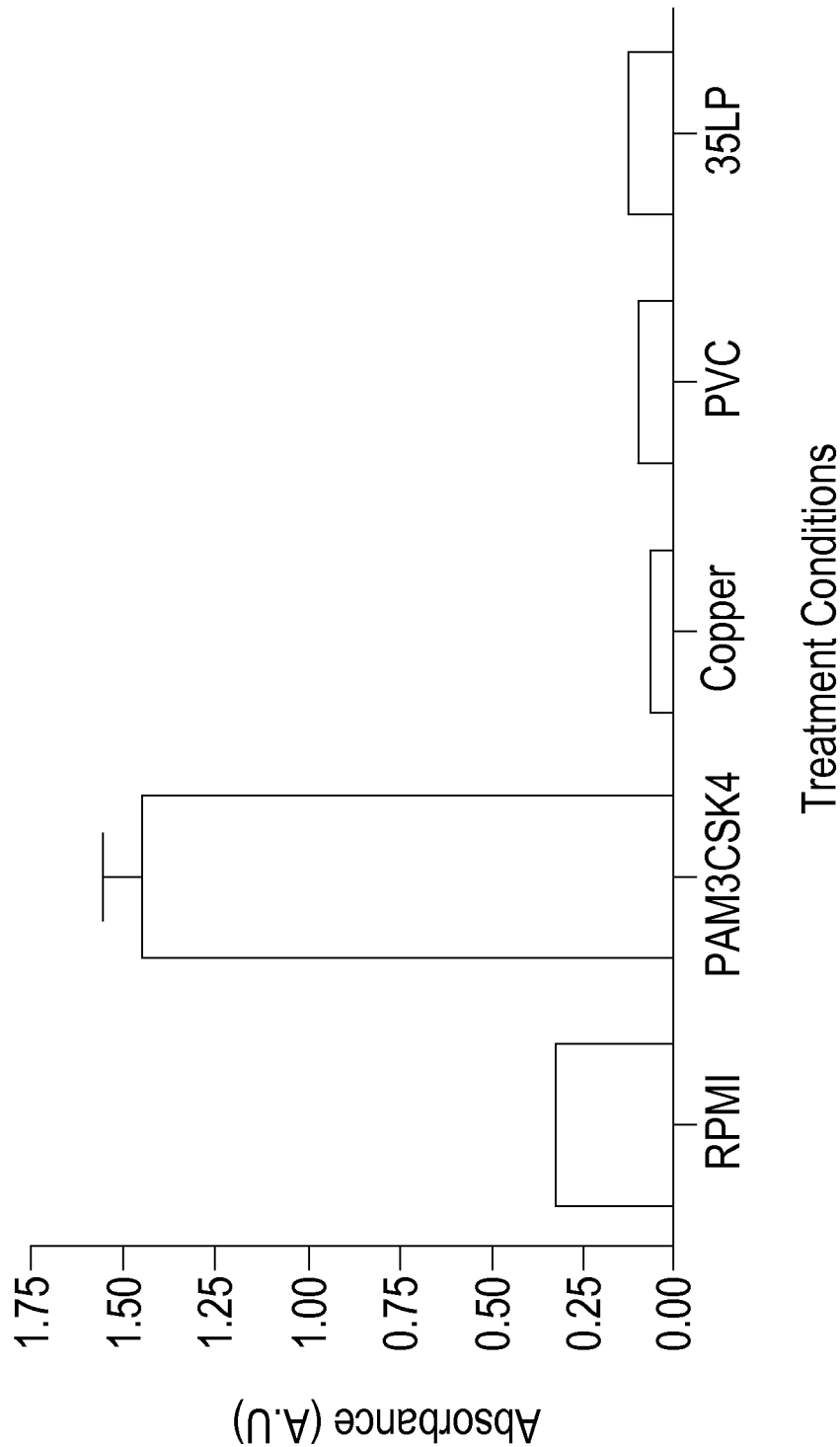
FIG. 2 is a graph depicting activation/suppression of the NF-KB pathway through the TLR-2 receptor. HEK-293 cells transfected with TLR-2 receptors were cultured in the presence of negative (RPMI) and positive (PAM3CSK4) controls and in the presence of media that had been incubated in contact with copper, polyvinylchloride (PVC) and the lumen of a Cook Advance 35LP balloon catheter, each shown as the average of four samples with three replicates each, taken from a first manufacturing lot identified herein as LOT 1, as described further in Example 1 below.

AP substrate development reactions were allowed to proceed for 3 hours at 37° C. in the $CO_2$ incubator. The presence of AP associated substrate color development was assessed using a Molecular Devices Spectra Max 250 colorimetric plate reader set to read absorbance at $OD_{655}$. After removing this initial 15 μL of cell culture supernatant from the TLR cell cultures, the cell culture plates were placed back into the incubator for additional 24-hours to allow us to secure a 48-hour time point too. At this time, another 15 μL aliquot of cell culture supernatant was removed from the respective TLR cell cultures and added to another 96 well micro titer plate containing 185 μL/well of Quick-Blue AP developer substrate. This substrate reaction was subsequently incubated for 3 hours at 37° C. in the $CO_2$ incubator. The Quick-Blue AP developer substrate was again read at $OD_{650}$ on the Molecular Devices Spectra Max 250 colorimetric plate reader to quantitate the relative levels of SEAP production. Again, the level of SEAP reporter enzyme secretion is correlated with the degree of TLR type receptor stimulation by leached device-tubing contaminants. The results are shown in FIGS. 1-2 (TLR2 testing) and FIGS. 3-4 (TLR4 testing). As shown in FIGS. 1-2, which show averaged and individual replicate values, respectively, TLR2 was activated in the positive control (PAM3CSK4) relative to the negative control (RPMI). In the test articles, copper-, PVC- and 35LP-conditioned media samples all suppressed TLR2 relative to the negative control, with the 35LP-conditioned samples suppressing to a lower extent than copper and PVC.

Figure 3:
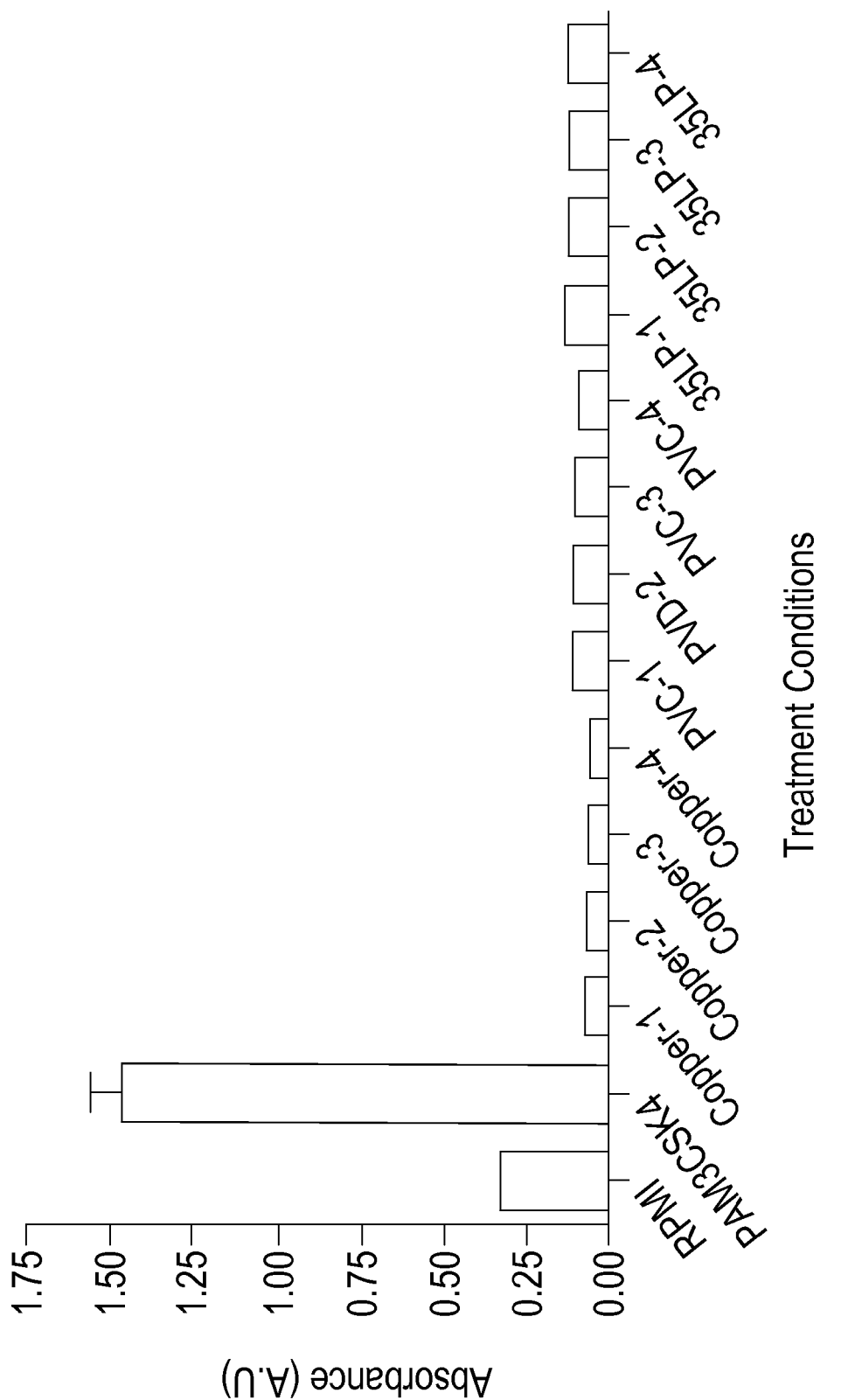
FIG. 3 is a graph depicting NF-KB activation/suppression levels in the individual replicates from LOT 1 used to generate FIG. 2, as described further in Example 1 below.
Figure 4:
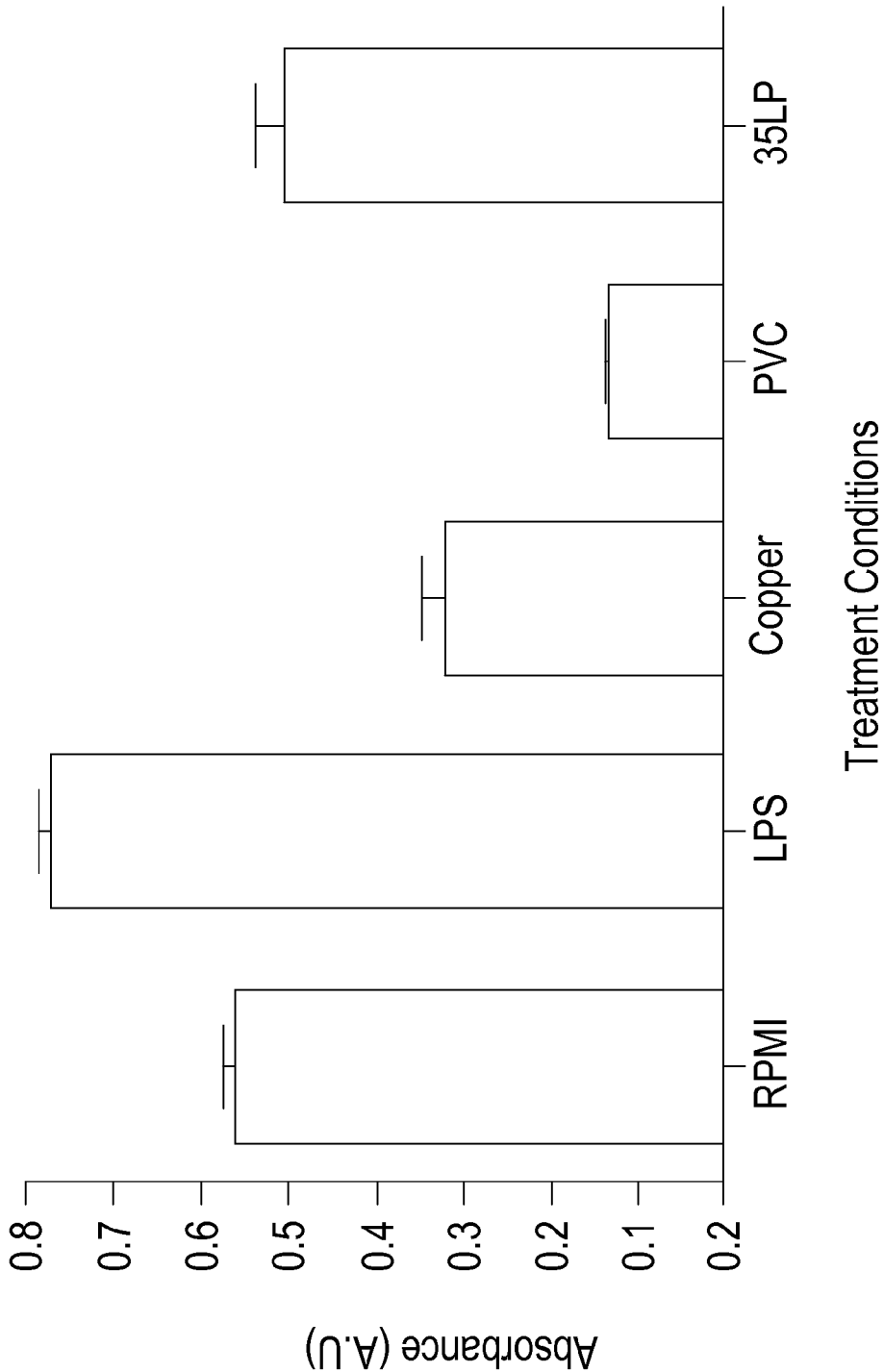
FIG. 4 is a graph depicting activation/suppression of the NF-KB pathway through the TLR-2 receptor. HEK-293 cells transfected with TLR-2 receptors were cultured in the presence of negative (RPMI) and positive (PAM3CSK4) controls and in the presence of media that had been incubated in contact with copper, polyvinylchloride (PVC) and the lumen of a Cook Advance 35LP balloon catheter, each shown as the average of four samples with three replicates each, taken from a second manufacturing lot identified herein as LOT 2, as described further in Example 1 below.
Figure 5:
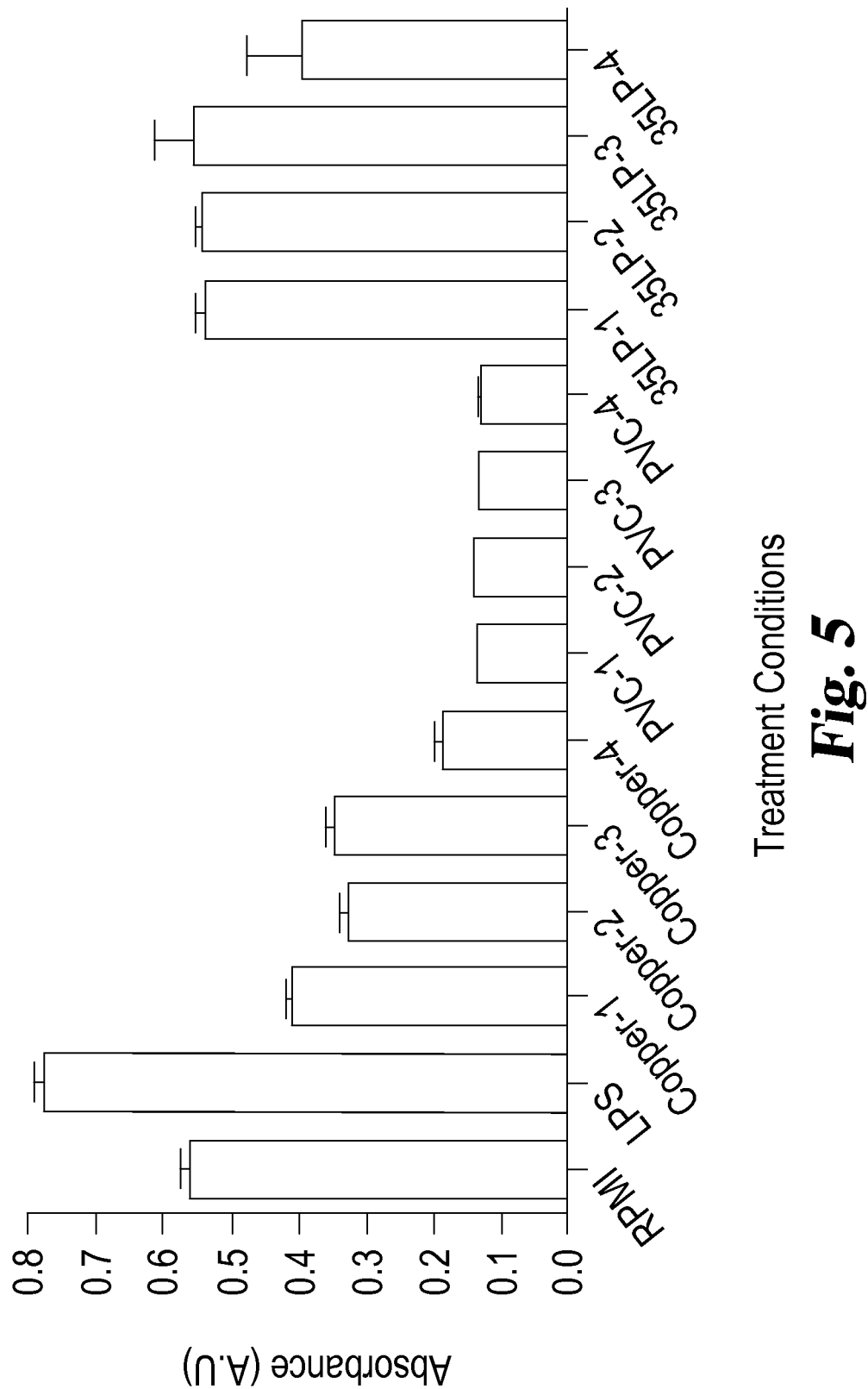
FIG. 5 is a graph depicting depicting NF-KB activation/suppression levels in the individual replicates from LOT 2 used to generate FIG. 4, as described further in Example 1 below.
Figure 6:
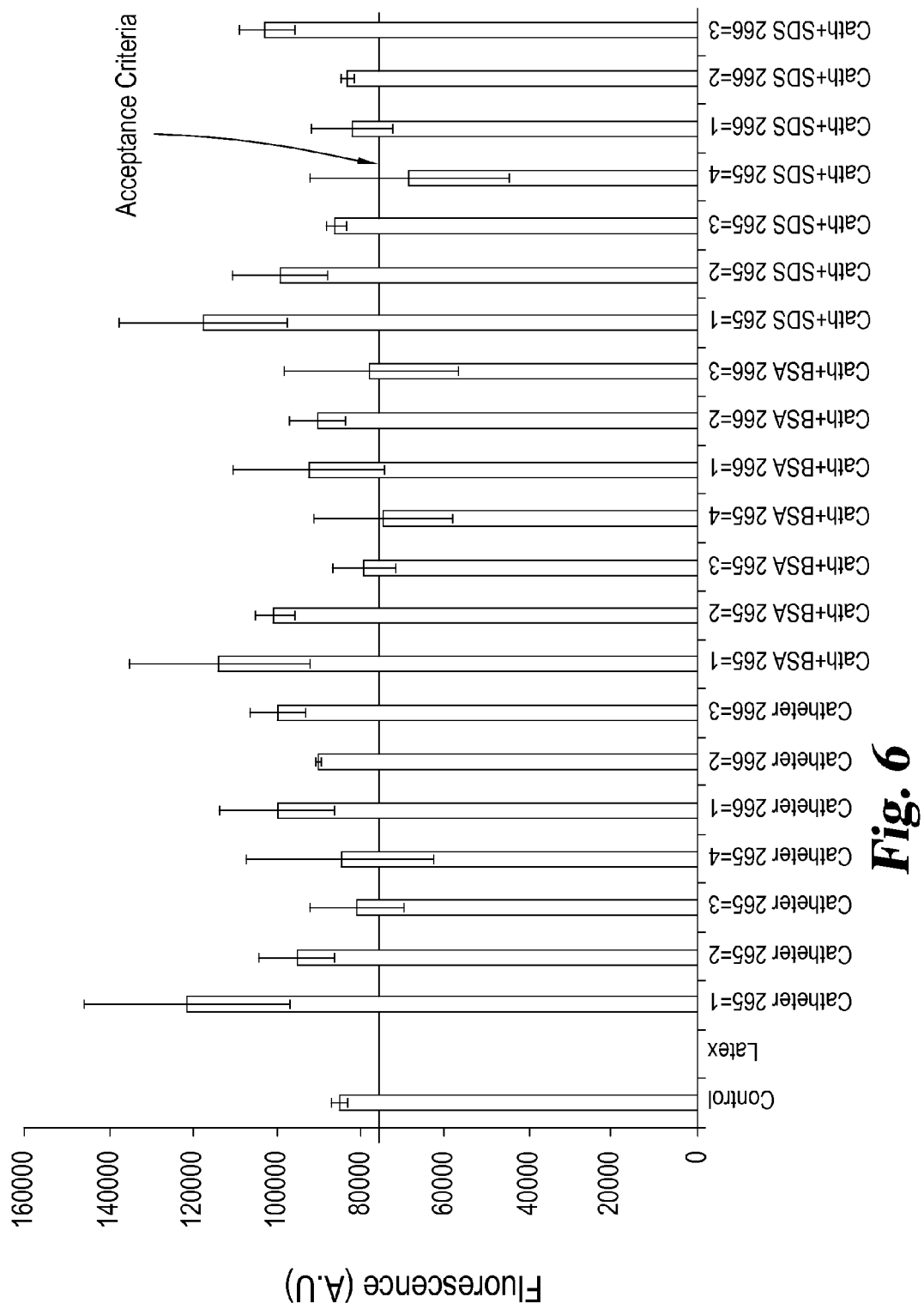
FIGS. 6 and 7 are graphs depicting the metabolic activity and total cytotoxic response of U937 cells after culture in the absence of applied condition (Control), in presence of media incubated in the presence of latex (used as a positive control), or in the presence of media incubated in the lumens of replicate 35 LP samples taken from LOT 1 and LOT 2 for purposes of metabolic activity and cytotoxicity testing (the replicate 35LP samples for this metabolic activity and cytotoxicity testing were new samples as opposed to re-used samples from TLR testing noted above; the incubated media from each 35LP replicate was split into separate aliquots and used for the separate assays).
Figure 7:
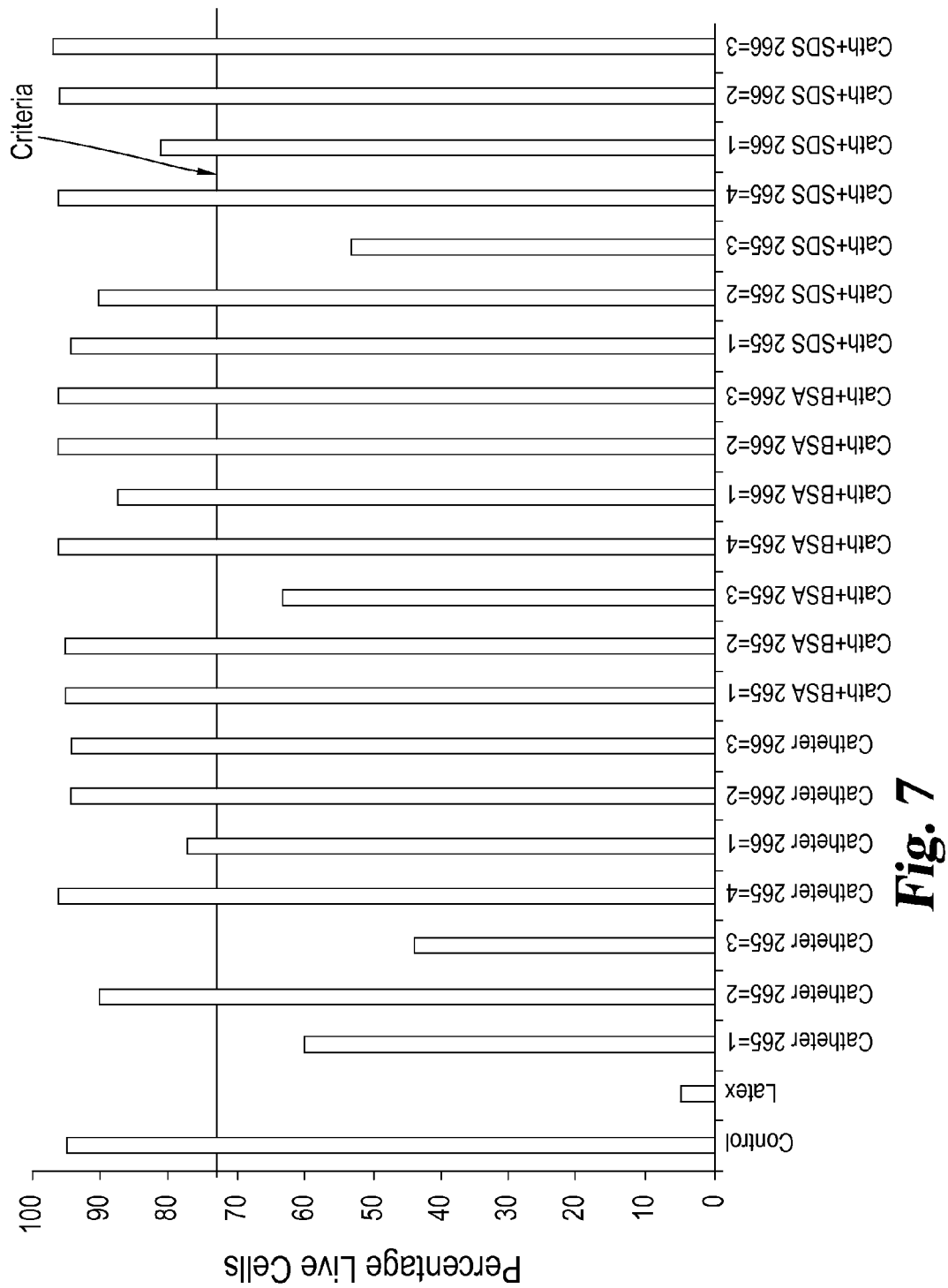

The results for TLR4 shown in FIGS. 3-4 were similar to those for TLR2. TLR4 was activated in the positive control (LPS) relative to the negative control (RPMI). In the test articles, copper-, PVC- and 35LP-conditioned media samples all suppressed TLR4 relative to the negative control, with the 35LP-conditioned samples suppressing to a lower extent than copper and PVC.

EXAMPLE 2

Metabolic Activity and Cytotoxicity Assays

This Example describes cell based assays for assessment of catheter lumens for their effect on the metabolic activity of cells or for potential cytotoxicity to cells. Specifically herein, U937 cells were used for these purposes.
Materials
U937 cells were obtained from ATCC (ATCC CRL-1593.2).
Cook Advance 35 LP balloon catheters from two different device lots (designated LOT 1 and LOT 2) were obtained from Cook Medical, Bloomington, Ind.
Culture media for the U937 cells was obtained from ATCC. ATCC complete growth medium was prepared for culturing these cells by adding a total concentration of 10% fetal bovine serum to ATCC formulated RPMI-1640 medium (Cat #30-2001) and 100 units/mL penicillin and 100 μg/mL streptomycin. The cells were cultured in 95% air, 5% $CO_2$ in a humidified atmosphere at 37° C.
Latex tubing (positive control) was commercially obtained.
Methods
Test Media:
Approximately 1 mL of the U937 cell culture medium was incubated in contact with the 35 LP catheters and the latex (positive control) for 48 hours at human physiologic temperature (37° C.). For the 35 LP catheters, the guidewire lumen of each catheter was filled completely by injecting a volume of about 1 mL of the culture medium into the lumen, after which the lumen was clamped off at each end with parafilm and the catheter incubated in a 37° C. incubator for 48 hours. After the incubation period, the conditioned samples of culture media were collected in 15 ml conical tubes, for prompt use in the metabolic activity and cytotoxicity assays.
Initial Cell Culture: U937 cells were cultured at passage 7 or 8 in T75 cell culture flasks at approximately $5 \times 10^5$ cells per mL. After aspirating the cells into a 50 ml conical tube they were centrifuged at 300×g for 5 minutes at room temperature. Following this the supernatant was removed and the pellet was resuspended in fresh media to give a cell concentration of $1 \times 10^6$ cells/mL. An aliquot that gave $1 \times 10^6$ cells was aspirated into a 12×75 mm polystyrene tube with a cap and the tubes were centrifuged at 300×g for 5 minutes at room temperature. The media was aspirated following centrifugation and tubes were racked to loosen the pellet. One mL of either the device exposed or latex tube exposed treatment media was added to the pellet in their respective tubes whereas untreated media was added to the control tubes and the tubes for staurosporine. The cells were then transferred to a 24 well plate for an incubation period of about 5 hours after which the 2 different assays were performed.
Presto Blue Assay: The Presto Blue assay was set to be read at 5 hours after the staurosporine was added to its well. Using cells from the control wells a standard curve was made with cell culture media: media alone (blank); 31,300; 62,500; 125,000; 250,000 and 500,000 cells. 90 μl of each standard and treatment groups were placed in triplicate, in a 96 well plate followed by addition of 10 μl of the Presto Blue reagent to every well. The plate was covered and placed into a 37° C. incubator for 30 minutes. The plate was read on a fluorescence plate reader following this incubation.
Cell Viability/Cytotoxicity Assay: 200 μl of cells from each treatment well were pipetted into a 12×75 mm polystyrene tube with a cap, in duplicate. FAM-FLICA an apoptosis detection probe was diluted with DMSO to a 150× stock concentrate solution. Prior to use a 1:7.5 dilution was prepared to obtain a 20× working solution. About 10 μl of this working solution was added to each tube except the unstained cells following which the tubes were left to incubate at 37° C. for 45 minutes. 2 mL of a 1% BSA in PBS solution was added to each tube including unstained after the incubation period. The tubes were then centrifuged at 300×g for 5 minutes at room temperature. Aspiration of the media followed and the tubes were racked to loosen the pellet. The above steps were repeated for a second wash. Finally 200 micro liters of a 1% BSA in PBS solution was added to each tube including unstained and set on ice prior to reading.
The results are shown in Figures.
The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

The invention claimed is:

1. A method for testing a material of construction of a lumen of a medical device for a potential effect of the lumen on cells delivered through the lumen, comprising:
    injecting a liquid medium into the lumen;
    incubating the liquid medium injected into the lumen in contact with a material of construction of a wall of the lumen;
    collecting the liquid medium from the lumen after said incubating to provide a collected liquid medium;
    contacting at least one cell with the collected liquid medium, wherein the at least one cell includes exogenous DNA encoding at least one toll-like receptor; and
    assessing the effect of said contact with a material of construction on the expression of the at least one toll-like receptor by the cell, so as to assess the lumen for a potential effect of the lumen on cells delivered through the lumen.

2. The method of claim 1, wherein the medical device is a catheter.

3. The method of claim 1, wherein the at least one cell is a population of cells, and wherein the population of cells is a clonal population.

4. The method of claim 1, wherein the cell is a mammalian cell.

5. The method of claim 1, wherein the cell is a human cell.

6. The method of claim 1, wherein the at least one toll-like receptor includes toll-like receptor 2, toll-like receptor 4, or both.

7. A method for testing a material of construction of a lumen of a medical device for a potential effect of the lumen on cells delivered through the lumen, comprising:
    first assessing the material of construction of the lumen while the lumen is intact for an effect of the lumen on innate immune response of a cell; and
    second assessing the material of construction of the lumen while the lumen is intact for an effect of the lumen on at least one other characteristic of a cell, said at least one other characteristic selected from cytotoxicity, motility, viability, and metabolic activity,
    so as to assess the lumen for a potential effect of the lumen on cells delivered through the lumen.

8. The method of claim 7, wherein the medical device is a catheter.

9. The method of claim 7, wherein said second assessing includes assessing the effect of the lumen on both cytotoxicity to a cell and metabolic activity of a cell.

10. A method for assessing a material of construction of a lumen of a medical device for a potential effect of the lumen on cells delivered through the lumen, comprising:
    contacting at least one cell with a liquid medium that has been incubated within the lumen in contact with a material of construction of a wall of the lumen; and
    assessing the effect of said contacting on at least one characteristic of the at least one cell, wherein the at least one characteristic includes an innate immune response of the cell,
    so as to assess the lumen for a potential effect of the lumen on cells delivered through the lumen.

11. The method of claim 10, wherein the medical device is a catheter.

12. The method of claim 10, wherein said at least one characteristic also includes metabolic activity.

13. A method for testing a lumen formed by components of an assembly for a potential effect of the lumen on cells delivered through the lumen, comprising:
    incubating a liquid medium within a lumen in contact with a wall of the lumen of a sample assembly including a sample first component coupled to a sample second component to form the lumen;
    collecting the liquid medium after said incubating to provide a collected liquid medium;
    contacting at least one cell with the collected liquid medium; and
    assessing the effect of said contacting on at least one characteristic of the cell,
    so as to assess the lumen for a potential effect of the lumen on cells delivered through the lumen.

14. The method of claim 13, wherein the first sample component is a catheter and the second sample component is a needle or syringe barrel.

15. The method of claim 13, wherein the cell is a mammalian cell.

16. The method of claim 13, wherein the cell is a human cell.

17. A kit manufacturing method including assessment of a passageway for a potential effect of the passageway on cells delivered through the passageway, comprising:
    manufacturing a first device lot including a plurality of units of a first delivery component each having a first lumen for passage of cells;
    manufacturing a second device lot including a plurality of units of a second delivery component each having a second lumen for passage of cells, wherein the first delivery component is associable with the second delivery component to provide a delivery assembly having a passageway for passing cells, the passageway including the first lumen and second lumen;
    sampling the first device lot to obtain first test sample units of the first delivery component;
    sampling the second device lot to obtain second test sample units of the second delivery component;
    associating one of said first test sample units with one of said second sample units to provide a sample delivery assembly having a passageway including the first lumen of the first test sample unit and the second lumen of the second sample unit;
    assessing the passageway for an effect of the passageway on at least one characteristic of a cell so as to assess the passageway for a potential effect of the passageway on cells delivered through the passageway; and packaging first delivery components from the first device lot with second delivery components from the second device lot.

18. The method of claim 17, wherein said assessing comprises:

passing cells through the passageway;

recovering the cells after said passing; and assessing the recovered cells for an effect of the passageway on at least one characteristic of the cells.

19. The method of claim 17, wherein said assessing comprises:

incubating a liquid medium in contact with a wall of the passageway, said wall including wall portions from the first lumen and wall portions from the second lumen, to form a treated medium; and contacting cells with the treated medium.

20. The method of claim 17, also comprising, prior to said packaging, determining that said sample delivery assembly meets at least one predetermined criterion related to said effect on at least one characteristic of a cell.

* * * * *